US00PP22471P2

(12) United States Plant Patent
Bradford

(10) Patent No.: US PP22,471 P2
(45) Date of Patent: Jan. 31, 2012

(54) NECTARINE TREE NAMED 'PEARL TIME'

(50) Latin Name: *Prunus persica*
Varietal Denomination: Pearl Time

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/928,442

(22) Filed: Dec. 13, 2010

(51) Int. Cl.
*A01H 5/00* (2006.01)

(52) U.S. Cl. ..... Plt./189

(58) Field of Classification Search ..... Plt./189, Plt./188
See application file for complete search history.

(56) References Cited

U.S. PATENT DOCUMENTS

| | | | |
|---|---|---|---|
| PP7,507 | P | 4/1991 | Bradford |
| PP12,570 | P2 | 4/2002 | Bradford |
| PP16,034 | P3 | 10/2005 | Bradford |

*Primary Examiner* — Kent L Bell

(57) ABSTRACT

The present invention relates to a new and distinct variety of nectarine tree, *Prunus persica,* broadly characterized by a medium size, moderately vigorous, half-hardy, self-fertile, very productive and regular bearing tree. The variety blooms during the early to mid season and requires about 500 chilling hours. The fruit matures under the ecological conditions described in mid to late June, with first picking on Jun. 22, 2010. The fruit is uniformly medium in size, globose in shape, freestone in type, firm and melting in texture, white in flesh color, mostly red in skin color, and sub-acid and very sweet in flavor.

1 Drawing Sheet

Botanical classification: *Prunus persica.*
Variety denomination: 'Pearl Time'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Pearl Time'.

The present variety was hybridized by me during the 2000 blooming season as a first generation cross using 'Snow Princess' (U.S. Plant Pat. No. 12,570) peach as the selected seed parent and 'Spring Bright' (U.S. Plant Pat. No. 7,507) nectarine as the selected pollen parent. The fruit of this cross was gathered that summer of 2000, and the seeds were removed from the fruit, germinated, stratified, and grown as seedlings on their own root in my greenhouse. Upon reaching dormancy that winter, the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. After its initial selection in 2004, the present variety was carefully observed and further evaluated during each subsequent fruiting season. As part of this testing process, I asexually reproduced the present nectarine variety by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Snow Princess' peach by producing fruit that is white in flesh color, freestone in type, sub-acidic and sweet in flavor, and firm in texture, but is quite distinguished therefrom by producing fruit that is nectarine instead of peach and by maturing about forty days earlier.

The present variety is similar to its pollen parent, 'Spring Bright' nectarine by requiring about 500 hours of dormant chilling, by blooming in the early to mid season, and by producing fruit that is full red in skin color, firm in texture, globose in shape, and medium in size, but is quite distinguished therefrom by producing nectarines that are white instead of yellow in flesh color, freestone instead of clingstone in type, sub-acidic instead of acidic in flavor, and that mature about six days earlier.

The present variety is most similar to 'Spring Pearl' (U.S. Plant Pat. No. 16,034) nectarine by producing fruit that is white in flesh color, almost full red in skin color, firm in texture, sub-acidic in flavor, and that matures in mid to late June, but is distinguished therefrom by requiring less chilling hours, by blooming earlier, by having globose instead of reniform leaf glands, and by producing fruit that is freestone instead of clingstone in type, that is sweeter in flavor, and that matures about five days earlier.

SUMMARY OF VARIETY

In summary, the present nectarine variety is characterized by a medium size, moderately vigorous, half-hardy, self-fertile, very productive and regular bearing tree. The variety blooms during the early to mid season and requires about 500 chilling hours. The fruit matures under the ecological conditions described in mid to late June, with first picking on Jun. 22, 2010. The fruit is uniformly medium in size, globose in shape, freestone in type, firm and melting in texture, white in flesh color, mostly red in skin color, and sub-acid and very sweet in flavor.

DRAWING

The accompanying photograph consists of four whole fruits positioned to display the characteristics of the skin color and form, one divided fruit to reveal the flesh and stone, two insets to reveal buds and a blossom, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 25, 2010, on the original tree during its tenth growing season. The blossom and flower descriptions were made the previous blooming season. All major color code designations are by reference to the Inter-Society Color Council, National Bureau of Standards. Common color names are also used occasionally.

It is to be noted that the climatic conditions in 2010 led to delayed fruit ripening for most of the season by approximately ten days. This should be taken into account when comparing to other variety descriptions made referencing different years. However, the relative blooming times and ripening times cited in this application are accurate for 2010, and should remain about the same in future years.

Parentage

Seed parent: 'Snow Princess' peach (U.S. Plant Pat. No. 12,570).

Pollen parent: 'Spring Bright' nectarine (U.S. Plant Pat. No. 7,507).

Tree

Size: Medium, reaching and maintaining a height of 10' [3.05 m.] and a spread of 10' [3.05 m.] after six growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Half-hardy with respect to central California winters.

Approximate chilling requirement: 500 hours.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

- *Size.*—Medium, reaching a maximum diameter of 5⅞" [149.2 mm.] after the tenth growing season.
- *Texture.*—Shaggy.
- *Bark color.*—A Dark grayish yellowish brown [81. d.gy.yBr] and Dark grayish brown [62. d.gy.Br] variegation with Moderate brown [58. m.Br] crevices present.
- *Lenticels.*—Approximate Number Per Square Inch: 15. Color: Dark orange yellow [72. d.OY]. Average Size: ⅜" [9.5 mm.]. Shape: Eye-shaped, elongated.

Branches:

- *Size.*—Diameter of limb is 2¾" [69.9 mm.] measured 12" above the crotch, 1¾" [44.5 mm.] measured 12" above the first fork.
- *Texture.*—Smooth on first year wood, increasing roughness with age.
- *Color.*—1st Year Wood Topside: Grayish red [19. gy.R]. 1st Year Wood Underside: Brilliant yellow green [116. brill.YG]. Second Year Wood: Deep yellowish brown [75. deep yBr]. Older Wood: A Moderate brown [58. m.Br] and Dark grayish brown [62. d.gy.Br] variegation.
- *Lenticels.*—Number Per Square Inch: About 60 on second year wood. Color: Light yellowish brown [76. l.yBr]. Average size: 1/16" [1.6 mm.] on second year wood. Shape: Eye-shaped, elongated.

Leaves:

- *Size.*—Medium. Average Length: 5½" [139.7 mm.]. Average Width: 1½" [38.1 mm.].
- *Arrangement.*—Alternate.
- *Thickness.*—Medium.
- *Form.*—Elliptical.
- *Apex.*—Acuminate.
- *Base.*—Acute, with an average base angle of 80 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: ½" [12.7 mm.]. Average Thickness: 1/16" [1.6 mm.]. Color: Brilliant yellow green [116. brill.YG].
- *Stipules.*—Number: Usually 2 per leaf, up to 6 per growing tip. Average Length: ¼" [6.4 mm.]. Color: Brilliant yellow green [116. brill.YG] becoming Moderate reddish brown [43. m.rBr] with maturity.
- *Glands.*—Number: 2 to 4 per leaf. Position: Mostly opposite, located on petiole and base of blade. Size: Small. Form: Globose. Color: Light yellow green [119. l.YG] becoming Dark reddish brown [44. d.rBr] with age.
- *Leaf buds.*—Pointed, medium in size.

Flower buds:

- *Hardiness.*—Half-hardy, with respect to central California winters.
- *Diameter.*—Typically ⅜" [9.5 mm.] 1 week before bloom.
- *Length.*—Typically 11/16" [17.5 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, about thirty stamens, five sepal and petal locations alternately positioned.

- *Type.*—Showy, large.
- *Average flower diameter.*—1⅞" [47.6 mm.].
- *Number of petals.*—Usually five, extra petal fragments are occasionally observed.
- *Petal shape.*—Circular to oval.

*Petal margin.*—Entire, slightly wavy.
*Average petal diameter.*—¾" [19.1 mm.].
*Average petal length.*—11/16" [17.5 mm.].
*Petal apex.*—Rounded.
*Petal base.*—Truncate.
*Petal color.*—Light pink [4. l.Pk] toward the apex, Strong pink [2. s.Pk] toward the base on both sides.
*Anther color.*—Deep reddish orange [36. deep rO] over a Light yellow [86. l.Y] center at bloom onset.
*Stigma color.*—Pale yellow green [121. p.YG].
*Sepal color.*—Dark purplish red [259. d.pR] on the outer surface.
*Sepal length.*—¼" [6.4 mm.].
*Sepal width.*—3/16" [4.8 mm.].
*Sepal apex.*—Rounded to elliptical to match the sepal length and width.
*Sepal margin.*—Fairly smooth.
*Average pistil length.*—¾" [19.1 mm.].
*Average stamen length.*—9/16" [14.3 mm.].
*Fragrance.*—Moderate.
*Blooming period.*—Early to mid seasonal, two days before 'Spring Bright' (U.S. Plant Pat. No. 7,507) nectarine.
*Onset of bloom.*—One percent on Feb. 17, 2010.
*Date of full bloom.*—Feb. 28, 2010.
*Duration of bloom.*—One to two weeks, dependent on ambient temperature.
*Number per cluster.*—1 to 3 with single flowers most common.

FRUIT

Maturity when described: Firm ripe, Jun. 25, 2010.
Date of first picking: Jun. 22, 2010
Date of last picking: Jul. 4, 2010
Size: Uniform, medium.
*Average diameter axially.*—2¾" [69.9 mm.].
*Average diameter across cheek plane.*—2⅞" [73 mm.].
*Average diameter across suture plane.*—2⅞" [73 mm.].
*Typical weight.*—6.7 ounces [189.94 grams].
Form: Uniform, symmetrical.
*Longitudinal section form.*—Round to slightly oval.
*Transverse section through diameter.*—Round.
Suture: Extends from the base, along the side, and ends just past the pistil point.
*Near the base.*—A sharp groove inside the cavity.
*Along the side.*—A shallow trough.
*Near the apex.*—A moderate groove.
Ventral surface: Rounded, lipped strongly toward the apex on both sides.
Lips: Equal toward the apex, slightly unequal along the side.
Cavity: Flaring, elongated in the suture plane, suture showing on both sides, Yellowish white [92. yWhite] stem markings typical.
*Depth.*—½" [12.7 mm.].
*Breadth.*—1⅛" [28.6 mm.].
Base: Somewhat truncate, cordate if viewed parallel to the suture.
Apex: Rounded, cordate if viewed parallel to the suture.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—Slight.
*Color.*—Dark red [16. d.R] over a Very red [11. v.R] background with Light orange yellow [70. l.OY] freckling on the sides and even stronger toward the apex.
Flesh:
*Color.*—White [263. White] toward the skin, Greenish white [153. gWhite] near the stone, and a very slight amount of Deep pink [3. deep Pk] bleeding close to the stone.
*Surface of pit cavity.*—Covered with Pinkish white [9. pkWhite] broken fibers when twisted from the stone.
*Amygdalin.*—Scarce.
*Juice.*—Moderate, rich.
*Texture.*—Very firm, tough, melting.
*Fibers.*—Abundant, fine, tender.
*Ripens.*—Slightly earlier at the apex.
*Flavor.*—Sub-acid and sweet, typically 18 to 22 brix.
*Aroma.*—Very slight.
*Eating quality.*—Very good.

STONE

Type: Semi-freestone at shipping ripeness, freestone when fully ripe.
Form: Oval.
Hilum: Narrow, oblong.
Base: Rounded.
Apex: Acuminate with a small, sharp ⅛" [3.2 mm.] tip.
Sides: Equal.
Surface: Irregularly furrowed and rigged near apex, pitted toward the base.
Ridges: Jagged.
External color: Light brown [57. l.Br].
Pit wall color when cracked: Light yellowish brown [76. l.yBr].
Cavity surface color: Light yellowish brown [76. l.yBr] with some Deep yellowish brown [75. deep yBr] areas.
Average pit wall thickness: ¼" [6.4 mm.].
Average width: 1 1/16" [27 mm.].
Average length: 1 7/16" [36.5 mm.].
Average breadth: ¾" [19.1 mm.].
Tendency to split: Slight.
Kernel:
*Form.*—Oval.
*Skin color.*—Pale yellow [89. p.Y] when first removed.
*Pellicle color.*—Yellowish gray [93. yGy].
*Vein color.*—Yellowish gray [93. yGy].
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition after 21 days in standard cold room at 36° Fahrenheit [2° Celsius].

Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Spring Pearl' (U.S. Plant Pat. No. 16,034) nectarine by producing fruit that is white in flesh color, almost full red in skin color, firm in texture, sub-acidic in flavor, and that matures in mid to late June, but is distinguished therefrom by requiring less chilling hours, by blooming earlier, by having globose instead of reniform leaf glands, and by producing fruit that is freestone instead of clingstone in type, that is sweeter in flavor, and that matures about five days earlier.

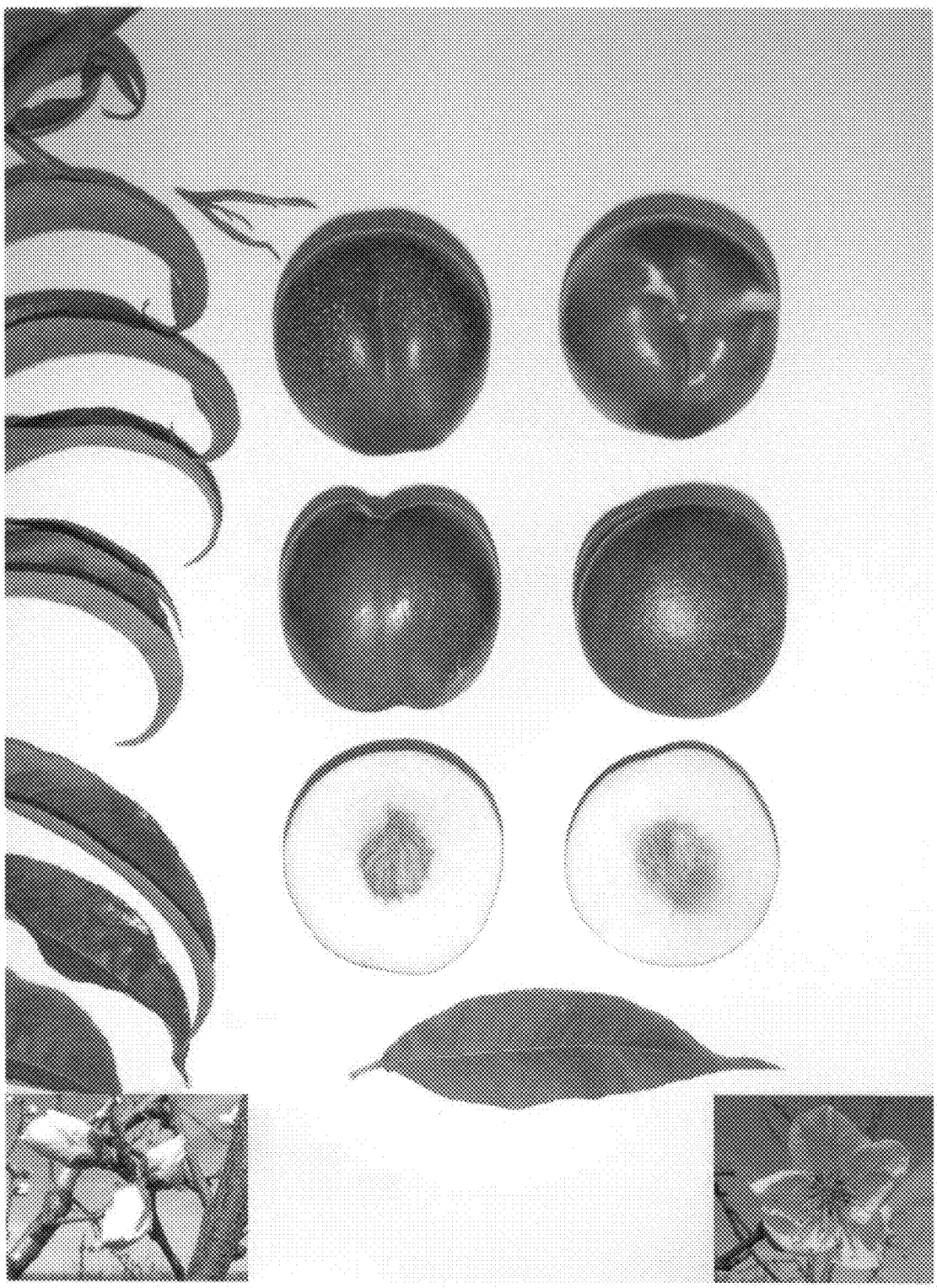

* * * * *